United States Patent [19]

Voss et al.

[11] 4,190,722
[45] Feb. 26, 1980

[54] 4,6-DI-O-(AMINOGLYCOSYL)-1,3-DIAMINOCYCLITOLS, PROCESS FOR THEIR PRODUCTION AND THEIR USE

[75] Inventors: Eckart Voss, Cologne; Peter Stadler, Haan; Uwe Petersen; Hans-Joachim Kabbe, both of Leverkusen; Karl G. Metzger, Wuppertal, all of Fed. Rep. of Germany

[73] Assignee: Bayer Aktiengesellschaft, Leverkusen, Fed. Rep. of Germany

[21] Appl. No.: 913,135

[22] Filed: Jun. 6, 1978

[30] Foreign Application Priority Data

Jun. 10, 1977 [DE] Fed. Rep. of Germany ....... 2726197
Jun. 10, 1977 [DE] Fed. Rep. of Germany ....... 2726208

[51] Int. Cl.² .................. A61K 31/71; C07H 15/22
[52] U.S. Cl. ................. 536/17 R; 424/180; 536/4
[58] Field of Search ................. 424/180; 536/17

[56] References Cited

U.S. PATENT DOCUMENTS

| 3,929,762 | 12/1975 | Umezawa et al. | 536/17 |
| 4,029,882 | 6/1977 | Wright | 536/17 |
| 4,048,430 | 9/1977 | Cooper et al. | 536/17 |
| 4,060,682 | 11/1977 | Umezawa et al. | 536/17 |
| 4,065,615 | 12/1977 | Horii et al. | 536/17 |

Primary Examiner—Johnnie R. Brown
Attorney, Agent, or Firm—Sprung, Felfe, Horn, Lynch & Kramer

[57] ABSTRACT

The invention includes selectively acylated or sulphenylated 4,6-O-(aminoglycosyl)-1,3-diaminocyclitols (and methods for their preparation). Also included in the invention are 1-N-acylated-derivatives, such as 1-N-formyl-sisomicin, useful because of the anti-bacterial effects (and methods for their procurement). The invention includes, furthermore, methods for the procurement of said 1-N-acylated or sulphenylated derivatives, compositions containing them and methods for their use.

14 Claims, No Drawings

4,6-DI-O-(AMINOGLYCOSYL)-1,3-DIAMINOCY-CLITOLS, PROCESS FOR THEIR PRODUCTION AND THEIR USE

The invention relates to new, selectively acylated or sulphenylated 4,6-di-O-(aminoglycosyl)-1,3-diaminocyclitols, which are used as intermediate products for the preparation of valuable new and known antibiotics, and a process for the preparation of the selectivity protected compounds.

The new acyl or sulphenyl derivatives of the 4,6-di-O-(aminoglycosyl)-1,3-diaminocyclitols are compounds of the general formula (I)

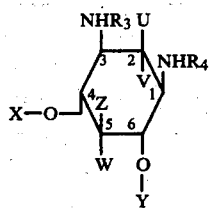

in which
X represents a radical of the formula

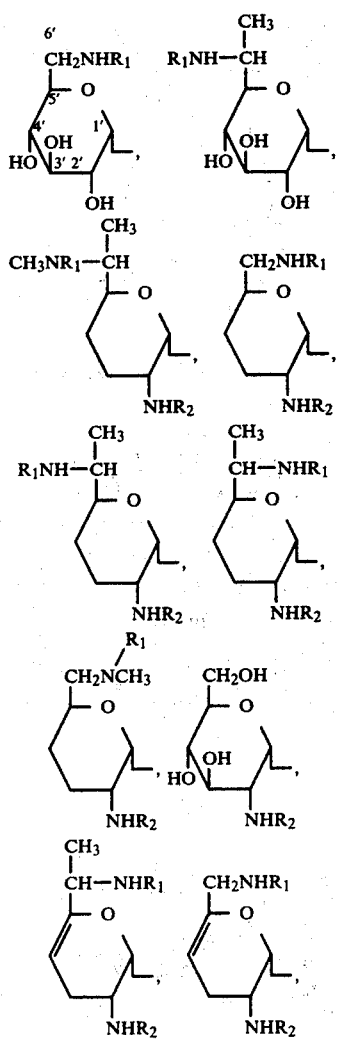

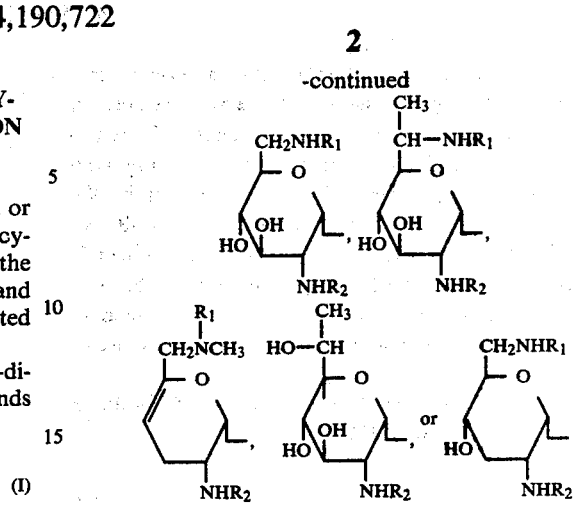

Y designates a radical

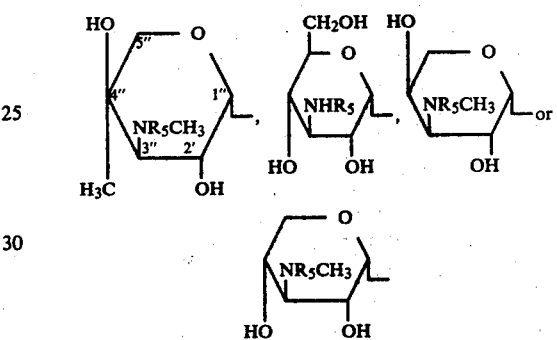

U, V and W are the same or different and each is hydrogen or hydroxyl and

Z is hydrogen, hydroxyl or amino, and $R_1$, $R_2$, $R_3$, $R_4$ and $R_5$ are each hydrogen or a radical —SR' or —CO—A with at least one being other than hydrogen wherein R' represents optionally substituted phenyl, or diphenylmethyl or triphenylmethyl and A designates a group —$(CH_2)_n$—B or

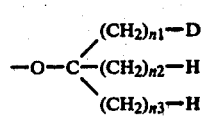

in which
B and D are the same or different and each is hydrogen or optionally substituted phenyl and n, $n_1$, $n_2$ and $n_3$ independently of one another represent a number from 0 to 5, R' which is "substituted phenyl" preferably represents a phenyl radical which is substituted by from one to three substituents each of which is nitro, $C_1$-$C_4$-alkyl, $C_1$-$C_4$-alkoxy, $C_1$-$C_4$-alkoxycarbonyl or phenyl or by from 1 to 5 halogen atoms, preferably chlorine atoms. Examples which may be mentioned are the o-nitrophenylsulphenyl radical and the 2,4,5-trichlorophenylsulphenyl radical.

B and D which are "substituted phenyl" preferably represent phenyl radicals which are substituted by one or two substituents each of which is nitro, $C_1$-$C_4$-alkyl, $C_1$-$C_4$-alkoxy or phenyl radicals or halogen atoms, preferably chlorine atoms.

The compounds, according to the invention, protected on the N atoms, of formula (I), which are derived from the antibiotics gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, tobramicin, G-418, 66-40B, 66-40D, JI-20A, JI-20B, G52, mutamicin 1, mutamicin 2, mutamicin 4, mutamicin 5 and mutamicin 6, which thus carry the radicals $R_1$, $R_2$, $R_3$, $R_4$ and $R_5$, defined as above, on the nitrogen atoms of these antibiotics, are of particular interest.

Of these compounds, the derivatives of sisomicin represented by formula (II)

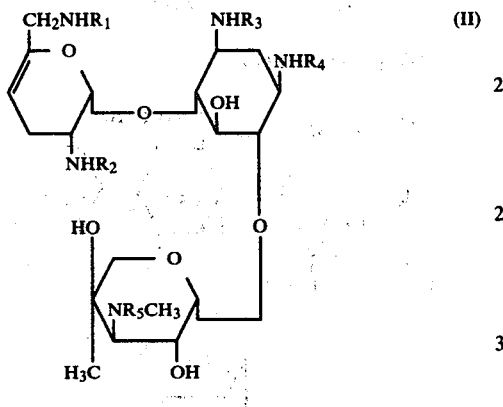

in which $R_1$, $R_2$, $R_3$, $R_4$ and $R_5$ have the meaning indicated above, are particularly valuable.

In addition, it has been found that the new selectively acylated or sulphenylated 4,6-di-(aminoglycosyl)-1,3-diaminocyclitols of the formula (I)

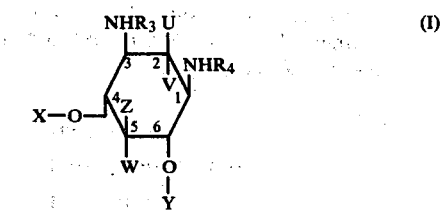

in which $R_3$, $R_4$, U, V, W, X, Y and Z have the meaning indicated above, are obtained when compounds of the formula (III)

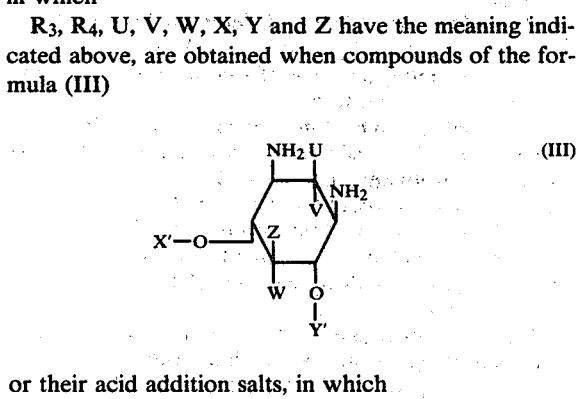

or their acid addition salts, in which

U, V, W and Z have the meaning indicated above and X' represents a radical

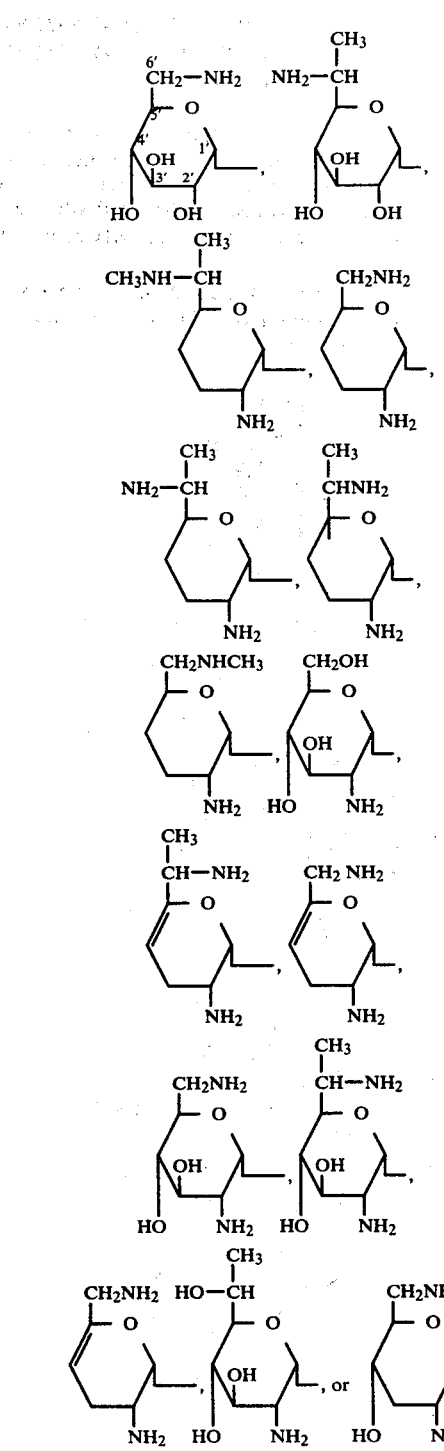

and Y' designates a radical

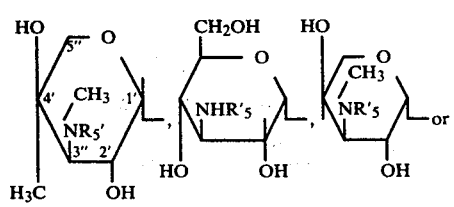

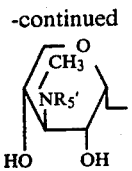

in which
R'₅ has the meaning indicated above for R₅, are reacted
(a) when one or more of R₁, R₂, R₃, R₄ and R₅ is a radical R'-S- with at least one of R₁, R₂, R₃, R₄ and R₅ being hydrogen, with about 3 to 4 equivalents of a compound of the formula (IV)

     (IV)

in which R' has the same meaning as defined hereinbefore in R₁, R₂, R₃, R₄ and R₅, and G designates halogen or a leaving group customary in sulphenylation reactions, preferably an activating ester radical, or
(b) when one or more of R₁, R₂, R₃, R₄ and R₅ is a radical A-CO-, with at least one of R₁, R₂, R₃, R₄ and R₅ being hydrogen, with about 3 to 4 equivalents of a compound of the formula (V)

     (V)

in which
A has the same meaning as defined hereinbefore in R₁, R₂, R₃, R₄ and R₅ with at least one of R₁, R₂, R₃, R₄ and R₅ being hydrogen and G' designates halogen or a leaving group customary in acylation reactions, preferably an activating ester radical, or a group —O—CO—A,
in which
A has the above meaning, in an inert solvent, optionally with the addition of water, generally at a temperature of from about −30° C. to +50° C., preferably from about 0° C. to +25° C., in the presence of a base, the reaction product being worked up in the customary manner as required.

If sisomicin and o-nitrophenylsulphenic acid p-nitrophenyl ester are used as starting materials, the course of the reaction (with preferred reaction conditions) can be represented by the following equation:

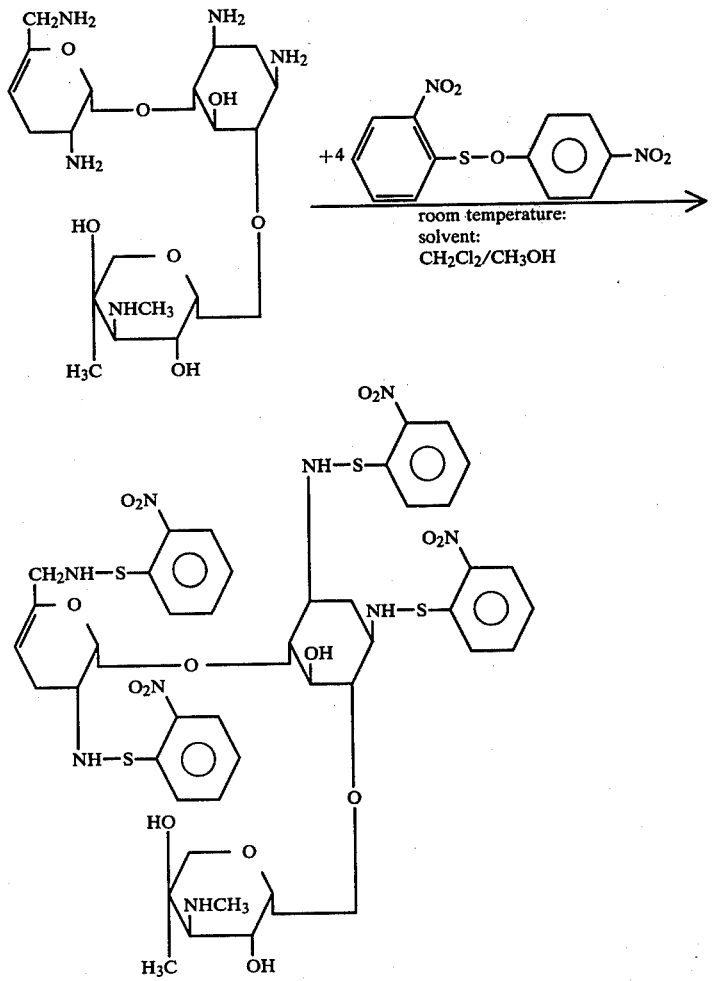

The compounds of the formula (IV) in which G designates chlorine or the p-nitrophenyloxy radical are preferably used for the preparation of the compounds of the formula (I) in the manner described above, by reacting the unprotected or partially protected 4,6-di-O-(aminoglycosyl)-1,3-diaminocyclitols of the formula (III) with a reagent of the formula (IV). Examples of compounds of the formula (IV) which may be mentioned are: tritylsulphenyl chloride, o-nitrophenylsulphenyl chloride, 2,4-dinitrophenylsulphenyl chloride, 2,4,5-trichlorophenylsulphenyl chloride, pentachlorophenylsulphenyl chloride and o-nitrophenylsulphenic acid p-nitrophenyl ester, 2,4-dinitrophenylsulphenic acid p-nitrophenyl ester, 2,4,5-trichlorophenylsulphenic acid p-nitrophenyl ester and pentachlorophenylsulphenic acid p-nitrophenyl ester.

These reactive sulphenic acid derivatives are either already known (see, for example, Houben-Weyl, Methoden der Organischen Chemie (Methods of Organic Chemistry), volume XV, 1, page 203–222, Georg Thieme Verlag, Stuttgart, 1974) or can be prepared by processes which are already known for the preparation of compounds of analogous structure.

Preferred starting materials of the formula (V) are those in which G' designates chlorine or the radical —O—CO—A, in which A has the meaning indicated above. Examples which may be mentioned are: acetic anhydride, acetyl chloride and di-t-butyl pyrocarbonate, and the use of dialkyl pyrocarbonates as blocking reagents is generally to be particularly preferred for the preparation of N-alkyl-oxycarbonyl derivatives of sisomicin.

Possible diluents for the reaction with sulphenic acid halides are both inert organic solvents, such as chloroform and toluene, but preferably water-miscible solvents, such as dioxane, dimethylformamide and dimethoxyethane, and their mixtures with water.

The reactions with activated esters of the above mentioned sulphenic acids are preferably carried out in inert organic solvents, such as $CHCl_3$, dimethylformamide or pyridine or mixtures of such solvents with alcohols, preferably methanol or ethanol. The acyl compounds according to the invention may be prepared in any desired inert organic solvent or in mixtures of organic solvents with water, and mixtures of methanol, ethanol or acetone with water are preferred.

Bases which can be employed are all the basic compounds customary in organic chemistry, such as, for example, triethylamine, pyridine or diazabicyclononenes however, alkali metal hydroxides or carbonates, such as, for example, sodium hydroxide solution or sodium carbonate, are preferably used.

The sulphenylations or acylations are usually carried out at a temperature of from about −30° C. to +50° C., preferably from about 0° to +25° C.

The reactions can be carried out either under normal pressure or under elevated pressure. In general, the reactions are carried out under normal pressure.

In the sulphenylation or acylation of the aminoglycosides, 1 mol of reagent is desirably employed for each $NH_2$ group to be reacted. It is also possible to employ a 2-fold to 3-fold excess of reagent for the preparation of aminoglycosides protected on five N atoms. The acid addition salts of the 4,6-di-O-(aminoglycosyl)-1,3-diaminocyclitols with inorganic and organic acids, preferably the chlorides and sulphates, can also be employed.

In this case, the amount of auxiliary base used should be varied according to the number of amino groups present in salt form.

The new compounds of the general formula (I) are valuable intermediate products useful in the preparation of derivatives of 4,6-di-O-(aminoglycosyl)-1,3-diaminocyclitols, in particular of derivatives of the antibiotics gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, tobramicin, antibiotic G-418 antibiotic 66-40B, antibiotic 66-40D, antibiotic JI-20A, antibiotic JI-20B, antibiotic G-52, mutamicin 1, mutamicin 2, mutamicin 4, mutamicin 5 and mutamicin 6.

These antibiotics are valuable substances for effectively combating bacterial infections. However, their high activity is frequently associated with a relatively high nephrotoxicity and ototoxicity; added to this is the development of resistance by the combated germs. For these reasons it is desirable to prepare derivatives of the aminoglycoside antibiotics having improved properties which may even make it possible to combat resistant germs, whilst having a low toxicity. Compounds such as 1-N-acetylsisomicin and 1-N-ethylsisomicin have been disclosed as substances with this type of improved property (DT-OS (German Published Specification) 2,437,160).

However, starting from unprotected sisom cin, the preparation of mono-N-substituted sisomicin derivatives proves to be difficult since five amino groups of comparable reactivity are present in the sisomycin molecule. Mixtures of differently substituted products are, therefore, always obtained which makes expensive chromatographic processes for isolating the desired product necessary.

The present invention describes a process for the preparation of derivatives of aminoglycoside antibiotics with one or two selectively unprotected amino groups, the nature of the protective groups being such that both alkylations and acylations on the free nitrogen atoms are possible and a subsequent gentle de-blocking can be carried out.

The use of the intermediate products, according to the invention, for the preparation of valuable new and known derivatives of 4,6-di-O-(aminoglycosyl)-1,3-diaminocyclitols is illustrated in the following text:

The 4,6-di-O-(aminoglycosyl)-1,3-diaminocyclitols according to formula (I) which carry an unprotected amino or methylamino group on the 3" C atom and/or on one of the C atoms 1, 2', 3 or 6' can be smoothly alkylated or acylated at the unprotected positions mentioned, N-(di)-mono-N-alkyl or N-(di)-mono-N-acyl derivatives of 4,6-di-o-(aminoglycosyl)-1,3-diaminocyclitols being formed.

The sulphenyl protective groups can be split off either by nucleophiles, such as for example, $H_2S$, thiophenol and the like, or by weak acids, that is to say under conditions under which the newly introduced acyl or alkyl radicals are stable. If acyl radicals, such as, for example, acetyl, ethoxycarbonyl or t-butoxycarbonyl groups, are used as protective groups, the de-blocking can be carried out with aqueous alkali metal hydroxide or alkaline earth metal hydroxide or with an acid, such as trifluoroacetic acid, perchloric acid or boron trifluoride etherate, in an organic solvent or a mixture of an organic solvent with water. In this case also, by appropriately choosing acyl protective groups and reagents for splitting them off, newly introduced alkyl or acyl radicals are not attacked during the de-blocking.

The selective splitting off of the protective groups can be carried out either with an equivalent amount of the reagent effecting the splitting off or with an excess, but preferably with a from 2 to 50-fold excess. The optimum reaction time here may be conveniently determined by thin layer chromatography.

For the preparation of 1-N-acetyl-sisomicin using an intermediate product according to the invention, the procedure is, for example, to react a protected sisomicin derivative of the formula (II) in which $R_1$, $R_2$, $R_3$ and $R_5$ designate the o-nitrophenylsulphenyl radical with 1 equivalent of p-nitrophenyl acetate in pyridine, to split off the o-nitrophenylsulphenyl protective groups with excess hydrogen sulphide in alcohol at pH 1–3 and to isolate 1-N-acetylsisomicin by treatment with a basic ion exchanger.

For the preparation of 2'-N-acetylsisomicin for example, 1 mol of a compound of the formula (II) in which $R_1$, $R_3$, $R_4$ and $R_5$ designate tert.-butoxycarbonyl radicals is reacted with 1 equivalent of acetic anhydride in methanol and, after the acylation reaction has ended, the protective groups are split off with excess boron trifluoride etherate in acetone and the 2'-N-acetylsisomycin formed is isolated by treatment with a basic ion exchanger. 1-N-Formylsisomycin can be particularly advantageously prepared. For this, 2', 3,3'', 6'-tetra-N-(o-nitro-phenylsulphenyl)-sisomicin which is obtainable by sulphenylating sisomicin or an acid addition salt thereof, is reacted with, preferably from about one to about 5 mols of a formylating agent, the o-nitrophenylsulphenyl groups are split off using desirably a nucleophilic reagent, especially a sulphur-containing, nucleophilic reagent, such as, for example, $H_2S$ or thiophenol, the reaction mixture being worked up in the customary manner to give the free 1-N-formyl derivative and this is then optionally converted into a salt thereof, especially a pharmaceutically acceptable salt.

Thus the present invention provides in a further respect a process for the preparation of 1-N-formylsisomicin or a salt thereof in which a compound of the following general formula II' or a salt thereof

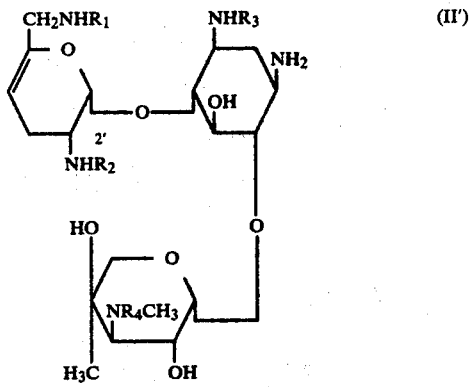

(II')

in which $R_1$, $R_2$, $R_3$ and $R_4$ are the same or different and each is hydrogen or an amino-protective group which can be easily split off is reacted with a formylating agent, and any protective group is split off, so as to produce 1-N-formylsisomicin or a salt thereof which is optionally converted into a salt thereof or into free 1-N-formylsisomicin, respectively.

The formylation of the sulphenyl derivative is generally carried out in an inert solvent, especially an organic solvent such as pyridine. If formic acid p-nitrophenyl ester is used as the formylating agent in the reaction described above, the course of the reaction can be represented by the following reaction equation:

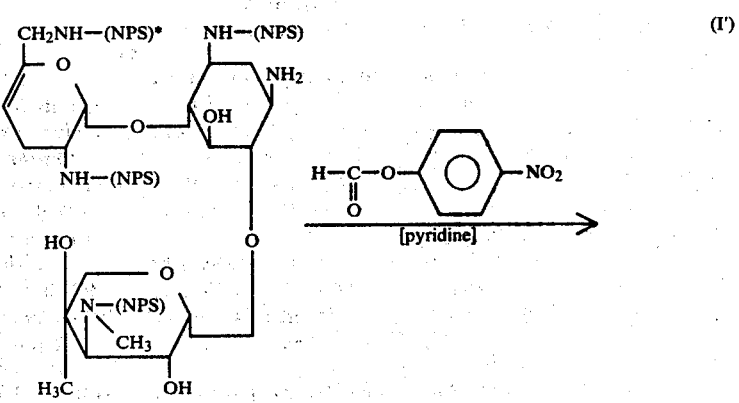

(I')

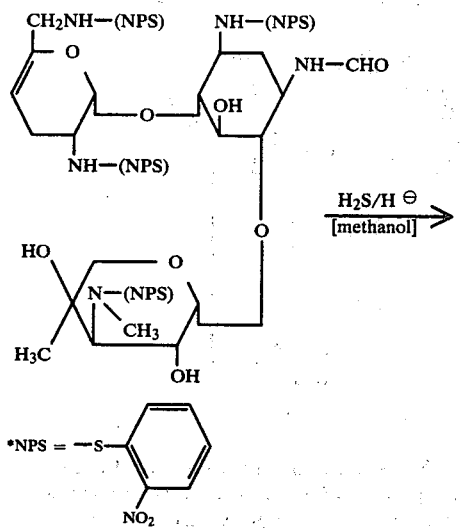

Instead of the o-nitrophenylsulphenyl derivatives, other sulphenyl derivatives, which are obtainable in an analogous manner by reacting sisomicin with a corresponding sulphenic acid chloride or a p-nitrophenyl ester of a sulphonic acid, can also be quite successfully employed. Examples which may be mentioned are: tritylsulphenyl-sisomicin, pentachlorophenylsulphenyl-sisomicin and 2,4-dinitrophenylsulphenyl-sisomicin derivatives.

Instead of p-nitrophenyl formate, formic acid-acetic acid anhydride is also particularly suitable for use in formylating the sulphenyl derivative.

The use of the intermediate products, according to the invention, for the preparation of new and known derivatives of 4,6-di-(aminoglycosyl)-1,3-diaminocyclitols consequently has a number of advantages. Thus, the intermediate products can be alkylated or acylated with high yields in a smooth reaction. After splitting off the protective groups, which is effected in a simple and gentle manner, the desired single end products are obtained, without expensive chromatographic purification operations becoming necessary.

As has already been mentioned hereinabove, the 4,6-di-O-(aminoglycosyl)-1,3-diaminocyclitol formyl derivative which is 1-N-formylsisomicin or a salt thereof can be particularly advantageously prepared from an appropriate intermediate according to the present invention. In further aspects the present invention provides 1-N-formylsisomicin, processes for its preparation and its use as a medicament, in particular as an antimicrobial agent.

Aminoglycoside antibiotics are important substances for effectively combating bacterial infections. However, the appearance of resistant germs in many cases lessens their wide applicability; moreover, side-effects, such as, for example, ototoxicity and nephrotoxicity, can occur. In some cases these disadvantages are successfully avoided by preparing derivatives.

Examples of aminoglycoside antibiotic derivatives of this type which are already known are 1-N-(4-amino-3-hydroxy)-butyrylkanamycin A, 1-N-acetylsisomicin and 1-N-ethylsisomicin (DT-OS (German Published Specification) 2,437,160).

It has now been found that 1-N-formylsisomicin (I')

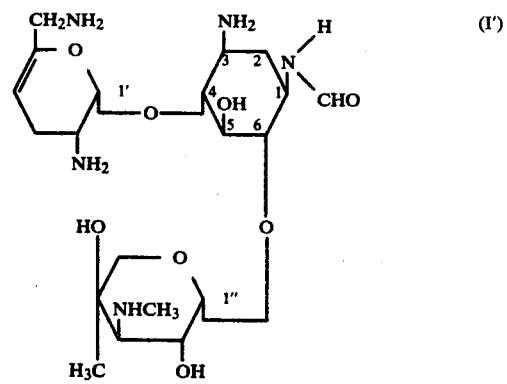

and its salts display powerful antibacterial properties against a number of germs.

Among the salts of the invention, those salts that are pharmaceutically acceptable are particularly important and are preferred. Suitable pharmaceutically usable salts are those derived from inorganic or organic acids, such as, for example, sulphuric, phosphoric, nitric, hydrochloric, hydrobromic, acetic, propionic, ascorbic or citric acid and the like.

In general, 1-N-formylsisomicin or a salt thereof can be prepared by a process in which a compound of the formula II'

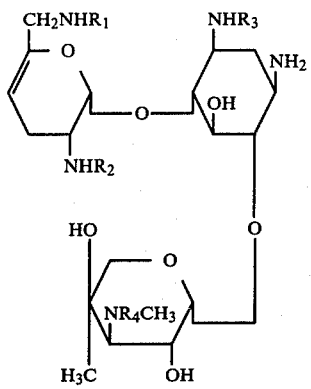

(II')

in which $R_1$, $R_2$, $R_3$ and $R_4$ are the same or different and each is hydrogen or an amino-protective group which can be easily split off, is reacted with a formylating agent, and any protective group is split off so as to produce 1-N-formylsisomicin or a salt thereof which is optionally converted into a salt thereof or into free 1-N-formylsisomicin, respectively.

The free 1-N-formylsisomicin of formula I' and its salts can be interconverted in any suitable manner; methods for such interconversion are known in the art. Thus the 1-N-formyl compound can be converted into its pharmaceutically usable salts by reaction with suitable acids, conveniently during the working up of the reaction products or subsequently thereto.

By protective groups which can be easily split off there are to be understood those protective groups which are used for protecting the amino groups in peptide syntheses and which can be removed again by alkaline or acid hydrolysis, mild hydrogenolysis or nucleophilic displacement reactions without influencing the sisomicin skeleton, the 1-N-formyl group introduced being retained. A number of such protective groups are known (Houben-Weyl, Methoden der Organischen Chemie (Methods of Organic Chemistry), volume XV 1, pages 46-305, Georg Thieme Verlag, Stuttgart, 1974). As may be seen in formula II', one or all of the N atoms 3, 2', 6' and 3" can be blocked; furthermore, it is also possible to use free sisomicin as the starting material.

Examples of N-protective groups which may be mentioned are the following radicals: o-nitrophenylsulphenyl, carbobenzoxy, phthaloyl, t-butoxycarbonyl, trifluoroacetyl, tosyl, p-nitrocarbobenzoxy and cyclopentyloxycarbonyl.

For the formylation reaction, a compound of the formula II' is reacted with, appropriately, at least 1 mol of a formylating agent, it being possible to use a one-fold to 10-fold, preferably from 1-fold to 5-fold, molar excess when the amino groups are correspondingly blocked, appropriately in the presence of an inert diluent—suitable diluents including organic solvents, such as, for example, dichloromethane, toluene, dimethylformamide, dimethylsulphoxide, pyridine and their mixtures with water and/or methanol—and optionally in the presence of an organic or inorganic base as an acid-trapping agent.

Suitable formylating agents are, in particular, formic acid p-nitrophenyl ester and the mixed anhydride of formic acid and acetic acid. However, in principle any other reactive formyl derivative can also be employed.

The reaction temperatures can be varied within a wide range. In general, the reaction is carried out at temperatures of from about −30° C. to +50° C., preferably from about 0° C. to +25° C.

A preferred process for the preparation of 1-N-formylsisomycin or a salt thereof, when $R_1$, $R_2$, $R_3$ and $R_4$ are all hydrogen, is the direct reaction of sisomicin, or a salt thereof with an inorganic or organic acid and with, generally about one mol, of a formylating agent in a manner which is in itself known, and subsequent separation of the desired 1-N-formyl derivative by chromatography.

Surprisingly, the 1-N-formylsisomicin according to the invention and its salts exhibit a higher action against resistant strains of bacteria, coupled with good tolerance, than do the compounds which are known from the state of the art. The substances according to the invention thus represent an enrichment of pharmacy.

The compounds according to the invention are antimicrobial agents with a broad spectrum of action and a particular activity against Gram-negative bacteria. These properties make it possible to use them as medicaments in combating bacterial diseases in warm-blooded animals. They are suitable for use in medicine in the prophylaxis and chemotherapy of local and systemic infections, in particular infections of the urogenital system, which are caused by Gram-negative bacteria, for example *E. coli*, Proteus, Klebsiella and Pseudomonas.

Inhibition depths in the agar hole test were found, for example, against the following strains of bacteria at a concentration of 100 micrograms/1 ml: *Pseudomonas aerug.* 5737, *Pseudomonas aerug.* F 41, *Klebsiella pneum.* 2 Munich, Klebsiella pneum. 1 Düsseldorf, E. Coli Münster and *E. coli* Neumann.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acids esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminum methahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from 20 to 2000, most preferably from 100 to 500, mg of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously or intravenously), rectally or topically, preferably orally, parenterally or topically. Preferred pharmaceutical compositions and medicaments are therefore those adapted for oral, parenteral or topical administration, such as tablets, capsules or elixirs, injection solutions or suspensions, or ointments, creams, or lotions, respectively. Administration in the method of the invention is preferably orally, parenterally to topically.

In general, it has proved advantageous to administer amounts of from 0.4 to 40, preferably from 2 to 10 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day. Thus, for example; injection solutions or suspensions are usually administered at a rate of 1 to 15 mg of active compound per kg of body weight in from 2 to 4 doses per day. Topical formulations containing, for example, from 0.1 to 3.0 g of the compound of the invention per 100 g of ointment cream or lotion are conveniently applied from 2 to 5 times daily.

In a further aspect the invention provides an animal feed containing a compound, composition or medicament according to the invention.

EXAMPLE 1

1,3,3'',6'-Tetra-N-(butoxycarbonyl)-sisomicin 450 mg of sisomicin are dissolved in 10 ml of water. After adding 10 ml of methanol, 870 mg of di-t-butyl pyrocarbonate are added, whilst stirring well. After stirring the mixture at room temperature for 1.3 hours, 5 ml of water are added, the mixture is filtered and the filtrate is evaporated to dryness in vacuo. The residue is dissolved in methanol and the desired product is precipitated by adding ether and petroleum ether. Yield = 600 mg.

13-C-NMR ($CD_2OD$): $\delta$=66.01 (C-3''); 52.23 (C-1); 51.67 (C-3); 48.23 (C-2'); 43.74 (C-6'); and 157.69(>c=o)ppm.

EXAMPLE 2

1,3,6'-Tri-N-(ethoxycarbonyl)-sisomicin 0.77 g of sisomicin is dissolved in 70 ml of water. 70 ml of ether are added and the mixture is cooled to 0° C. 1.75 ml of diethyl pyrocarbonate are now added dropwise, whilst stirring vigorously. After the addition has ended, the mixture is stirred at 0° C. for a further 10 minutes. The aqueous phase is then separated off, washed twice with 50 ml of ether each time and then evaporated to dryness in vacuo. 1.1 g of crude product are thus obtained, which are dissolved in 10 ml of methanol for purification; 20 ml of ether are added and the desired product is precipitated in this manner. $^{13}$C-NMR ($CD_3OD$): $\delta$=52.12 (C-1); 50.93 (C-3); 48.31 (C-2'); 43.66 (C-2'); 43.66 (C-6'); 158.98, 158.69 and 158.33 (>c=o) ppm.

EXAMPLE 3

1,2', 3,6'-Tetra-N-(ethoxycarbonyl)-sisomicin 1.1 g of sisomicin are dissolved in 50 ml of ethanol and 70 ml of water. After cooling to −10° C., 1.35 ml of diethyl pyrocarbonate are added dropwise to the solution, whilst stirring well. After a further 2½ hours at −10° C., 100 ml of water are added. The mixture is then extracted with 150 ml of petroleum ether and the aqueous phase is evaporated to dryness in vacuo. The residue is dissolved in methanol. The desired product is precipitated by adding excess ether and petroleum ether. Yield = 1.5 g (91%)

$^{13}$C-NMR($CD_3OD$/$CDCl_3$): $\delta$=50.86 (C-1); 49.90 (C-2); 46.33 (C-2'); 42.87 (C-6'); and 157.94, 157.73, 157.29 and 157.22 (>c=o)ppm.

EXAMPLE 4

1,2', 3,6'-Tetra-N-acetyl-sisomicin 1.1 g of sisomicin are dissolved in 120 ml of water. After adding 60 ml of methanol, 2.5 ml of acetic anhydride are added dropwise to the mixture, whilst stirring. After 15 minutes, the mixture is evaporated to dryness in vacuo. The residue is dissolved in 10 ml of methanol and this solution is added dropwise to a mixture of 30 ml of ether and 30 ml of petroleum ether, whereupon the desired product precipitates.

Yield = 1.43 g, mass spectrum: m/e=615. $^{13}$C-NMR ($CD_3OD$); $\delta$=50.14 (C-1); 49.20 (C-3); 46.88 (C-2'); 42.26 (C-6'); and 173.24, 173.13 and 172.63 (>c=o)ppm.

EXAMPLE 5

3''-N-p-Aminobenzylsisomicin 1.3 g of the product from Example 4 in 20 ml of dimethylformamide are stirred with 2.5 g of silver oxide and 2.2 g of p-nitrobenzyl bromide for 1 hour at room temperature. The mixture is then diluted with 50 ml of chloroform, stirred with a little wood charcoal for a short time and filtered. The filtrate is evaporated to dryness in vacuo and the residue is reprecipitated from chloroform using petroleum ether. Yield = 1.1 g.

In order to reduce the nitro group, 200 mg of the product obtained above are dissolved in 2 ml of water and, after adding 0.06 ml of acetic acid, 400 mg of iron powder are added to the mixture. The mixture is heated to 70° C. for 10 minutes and then allowed to react at room temperature for a further 1 hour. For working up, it is filtered, the filtrate is evaporated and the residue is decolorised in 5 ml of methanol and 5 ml of water using wood charcoal. After filtering the solution, the filtrate is evaporated in vacuo. In order to split off the N-acetyl groups, the residue thus obtained is heated under reflux in 2 ml of water with 1 g of barium hydroxide octahydrate for 8 hours. The mixture is allowed to cool and the barium salts are precipitated with carbon dioxide and filtered off. Evaporation of the filtrate and precipitation of the resulting residue from methanol using ether gives the title compound. Yield=95 mg.

EXAMPLE 6

2'-N-Acetyl-1,3,3'',6'-tetra-N-butoxycarbonyl-sisomicin 175 mg of 1,3,3'',6'-tetra-N-butoxycarbonyl-sisomicin are dissolved in 7 ml of methanol. 7 ml of acetone and 2 ml of acetic anhydride are successively added to this solution. After 2 hours, the mixture is freed from the solvent in vacuo and the residue thereby obtained is dissolved in methanol. The desired product is precipitated by adding excess ether and petroleum ether.

Yield = 170 mg. $^{13}$C-NMR ($CD_3OD$/$CDCl_3$): $\delta$=56.72 (C-2'); 23.14 and 175.80 (acetyl)ppm.

EXAMPLE 7

2'-N-Acetylsisomicin (method 1)

In order to split off the butoxycarbonyl protective groups, 150 mg of the product obtained according to Example 6 are dissolved in 3 ml of acetone, and 0.6 ml of a boron trifluoride/diethyl ether complex is added. After 1 hour, the mixture is poured into a mixture of 15 ml of ether and 5 ml of petroleum ether, whereupon the desired product precipitates. The product is deionised by stirring with a basic ion exchanger ($OH^\ominus$ form) in aqueous solution. The resin is filtered off and the filtrate is freed from solvent in vacuo. The residue is dissolved in a little methanol and precipitated by pouring into excess ether. Yield=60 mg. $^{13}$C-NMR ($D_2O$/dioxane): $\delta$=56.67 (C-2'); 21.62 and 177.01 (acetyl) ppm.

EXAMPLE 8

2'-N-Acetylsisomicin (method 2)

265 mg (0.25 mmol) of 1,3,3'',6'-tetra-N-nitrophenylsulphenyl-sisomicin and 47 mg of p-nitrophenyl acetate are stirred in 1.25 ml of absolute pyridine at room temperature for 1 hour, the solvent is evaporated off, the residue is taken up in 5 ml of dichloromethane, the dichloromethane solution is shaken with 5 ml of a methanolic hydrogen sulphide solution (saturated at 0° C.) and 0.7 ml of a saturated (20°) solution of HCl in methanol at room temperature for 1 minute, the reaction mixture is evaporated and the residue is digested with 20 ml of water. The digestion mixture is filtered, the filtrate is extracted by shaking twice with ether, the aqueous phase is filtered over 10 ml of a basic ion exchanger ($OH^\ominus$ form) and the filtrate is evaporated. The colourless evaporation residue consists of pure 2'-N-acetylsisomycin.

EXAMPLE 9

Penta-N-(o-nitrophenylsulphenyl)-sisomicin 38 g (0.20 mol) of o-nitrophenylsulphenyl chloride in 200 ml of dioxane, and 260 ml of 1 N NaOH are added to 13.84 g (20 mmols) of sisomycin sulphate in 100 ml of 1 N NaOH and 450 ml of freshly distilled dioxane, so that the pH is between 12 and 14. The precipitate is filtered off and dissolved in $CH_2Cl_2/H_2O$ and the $CH_2Cl_2$ phase is dried with $Na_2SO_4$.

$CH_2Cl_2$ is added to the filtrate, the aqueous phase is discarded and the organic phase is dried over $Na_2SO_4$. The combined organic phases are evaporated to dryness and filtered over 250 g of silica gel (column diameter 8 cm), first with $CH_2Cl_2$ and then with $CH_2Cl_2$/MeOH=97.5/2.5. After evaporating off the solvent, the eluate gives 22 g (91%) of penta-N-(o-nitrophenylsulphenyl)-sisomicin as an orange-coloured foam.

13-C-NMR($CDCl_3$): $\delta$=124-128 (aromatic H); 102.30 (C-1''); 99.00 (C-1'); 97.92 (C-4'); 89.05 (C-6); 82.33 (C-4); 57.31 (C-1) and 56.73 (C-3)ppm.

EXAMPLE 10

1,2',3,6'-Tetra-N-(o-nitrophenylsulphenyl)-sisomicin 13 g of o-nitrophenylsulphenic acid p-nitrophenyl ester are added to 4.5 g of sisomycin in 10 ml of methanol and 90 ml of dichloromethane and after 1 hour the reaction mixture is poured onto 300 ml of methanol, the precipitate is digested with 50 ml of dichloromethane and the insoluble product (3.6 g) is dried. The filtrate and digestion mixture are combined and chromatographed on a 6×15 cm $SiO_2$ column (running agent: dichloromethane with an increasing amount of methanol added, finally 10% of methanol).

After evaporating off the solvent, 3.4 g of 1,2',3,6'-tetra-nitrophenylsulphenyl-sisom cin (total yield 7.0 g=66%) and 2.5 g (21%) of penta-nitrophenylsulphenyl-sisomycin are isolated from the eluate.

13-C-NMR ($\delta$-6-DMSO): 63.87 (C-3''); 146.07, 145.28, 145.67 and 145.11 (in each case C-1 of the aromatic rings) ppm.

EXAMPLE 11

3''-N-(o-Nitrophenylsulphenyl)-sisomicin 160 ml of thiophenol are added to 16.0 g (13.2 mmols) of penta-N-nitrophenylsulphenyl-sisomicin in 80 ml of absolute pyridine and after 1 hour the mixture is poured onto 500 ml of diethyl ether, the precipitate is taken up in dichloromethane/methanol=8/2 and the solution is filtered over silica gel (column 5.5×12 cm, running agent dichloromethane/methanol=8/2, increasing addition of the running agent mixture methanol/dichloromethane/20 percent strength ammonia=4/2/1); after evaporating off the solvent, the red zone gives 6.6 g (83%) of 3''-N-o-nitrophenylsulphenylsisomicin as a deep red foam.

13-C-NMR($CD_3OD$): 33.59($CH_3N$); 52.23 (C-1); 51.16(C-3); 53 (C-2'); and 43.84 (C-6')ppm.

EXAMPLE 12

2',3,3'',6'-Tetra-N-(o-nitrophenylsulphenyl)-sisomicin and 1,2',3'',6'-tetra-N-(o-nitrophenylsulphenyl)-sisomicin 4.4 g (15.0 mmols) of o-nitrophenylsulphenic acid p-nitrophenyl ester in 85 ml of dichloromethane are added to 3.0 g (5.0 mmols) of 3''-N-nitrophenylsulphenyl-sisomicin in 5 ml of methanol and 45 ml of dichloromethane and the reaction mixture is immediately evaporated to dryness, the residue is taken up in dichloromethane and the solution is chromatographed on silica gel (column 5.5×30 cm) with 200 ml of dichloromethane and then with dichloromethane/methanol, (98/2)0.500 fractions are collected, 1,2',3'',6'-tetra-N-(o-nitrophenylsulphenyl)-sisom cin being obtained from the combined fractions 150 to 250 and the 2',3,3'',6'-tetra-N-(o-nitrophenylsulphenyl)-sisomicin being obtained from fractions 270 to 500, in each case as an orange-coloured foam.

1,2',3'',6'-Tetra-N-(o-nitrophenylsulphenyl)-sisomicin: $R_F$ ($CH_2Cl_2/CH_3OH$=9/1): 0.62 IR (KBr): 1,501, 1,360 and 1,300 (strong); 1.587, 1,562 and 755 (medium); and 1,442, 780 and 890 (weak).

2',3,3'',6'-Tetra-N-(o-nitrophenylsulphenyl)-sisomicin: $R_F$ ($CH_2CH/CH_3OH$=9/1): 0.42 IR (KBr): 1,500, 1,358 and 1,296 (strong); 1.586, 1,560 and 753 (medium); and 1,442, 890 and 779 (weak).

EXAMPLE 13

1,3,3'',6'-Tetra-N-(o-nitrophenylsulphenyl)-sisomicin 45 g of o-nitrophenylsulphenic acid p-nitrophenyl ester in 500 ml of dichloromethane are added to 9 g of sisomycin in 20 ml of methanol/180 ml of dichloromethane and the mixture is stirred at room temperature for 10 hours and evaporated to a volume of 100 ml and excess cyclohexane is added. The precipitate (37 g) is filtered off and dissolved in 150 ml of absolute pyridine, 200 ml of thiophenol are added to the mixture and, after 1 hour, this is poured onto 500 ml of diethyl ether. The precipitate is taken up in dichloromethane/methanol=8/2 and the solution is filtered over silica gel (column 5.5×12 cm, running agent dichloromethane/methanol=8/2, increasing addition of the running agent mixture methanol/dichloromethane/20 percent strength ammonia=4/2/1). The red zone is evaporated; 1,800 mg of the foam formed are dissolved in 3 ml of methanol and 27 ml of dichloromethane, 2.7 g of o-nitrophenylsulphenic acid p-nitrophenyl ester and 100 ml of methanol are added to the solution, the mixture is evaporated and the residue is chromatographed on 100 g of silica gel with dichloromethane/methanol (98/2). After evaporating, the yellow zone gives 1.5 g of 1,3,3″,6′-tetra-N-(o-nitrophenylsulphenyl)-sisomicin. $R_F$(CH$_2$Cl$_2$/CH$_3$OH=9/1): 0.37 13-C-NMR (d-6-dioxane): 124–147 (aromatic C) 146.8 (C-5′); 103.85 (C-1″); 102.40 (C-1′); 88.89 (C-6); and 76.48 (C-5) ppm.

EXAMPLE 14

1-Methoxyacetyl-sisomicin 265 mg (0.25 mmol) of 2′,3,3″,6′-tetra-nitrophenylsulphenyl-sisomicin and 58 mg of methoxyacetic acid p-nitrophenyl ester are stirred in 1.25 ml of absolute pyridine at room temperature for 1 hour and the solvent is evaporated off, the residue is taken up in 5 ml of dichloromethane, the dichloromethane solution is shaken with 5 ml of a methanolic hydrogen sulphide solution (saturated at 0°) and 0.7 ml of a saturated (20°) solution of HCl in methanol at room temperature for 1 minute, the reaction mixture is neutralised with a few drops of aqueous ammonia and evaporated and the residue is digested with 20 ml of water. The digestion mixture is filtered, the filtrate is extracted by shaking twice with ether, the aqueous phase is filtered over 10 ml of a basic ion exchanger (OH$^\ominus$ form) and the filtrate is evaporated. The colourless evaporation residue consists of pure 1-N-methoxy-acetyl-sisomicin.

$R_F$ (CHCl$_3$/CH$_3$OH/20% strength NH$_4$OH=2/4/1): 0.53 IR (KBr): 1,650, 1,105, 1,048 and 1,000 (strong).

EXAMPLE 15

1-N-Acetyl-sisomicin 265 mg (0.25 mmol) of 2′,3,3″,6′-tetra-nitrophenylsulphenyl-sisomicin are reacted with 47 mg of p-nitrophenyl acetate as described for 1-N-methoxyacetylsisomicin. After working up the reaction mixture, pure 1-N-acetylsisomicin is obtained in a completely analogous manner by evaporating the aqueous ion exchanger eluate.

13-C-NMR (CD$_3$OD): 23.03 (CH$_3$CO) 173.94 (C=O); 51.14 (C-3); 48.41 (C-2′); 150.62 (C-5′); 44.21 (C-6′) and 65.89 (C-3″).

EXAMPLE 16

3-N-Acetylsisomicin 265 mg (0.25 mmol) of 1,3,3″,6′-tetra-nitrophenylsulphenyl-sisomicin are reacted with 47 mg of p-nitrophenyl acetate as described for 1-N-acetylsisomicin. After identical working up of the mixture, pure 3-N-acetylsisomicin is isolated as the only product.

13-C-NMR(CD$_3$OD): 23.22 (CH$_3$CO), 173.13 (CO); 35.33 (C-2), 81.23 (C-4); 48.50 (C-2′); 148.42 (C-5′); 43.73 (C-6′) and 66.01 (C-3″).

EXAMPLE 17

3″-N-Acetylsisomicin 265 mg (0.25 mmol) of 1,2′,3,6′-tetra-nitrophenylsulphenyl-sisomicin are reacted with 47 mg of paranitrophenyl acetate as described for 1-N-acetylsisomicin. After identical working up of the mixture, pure 3″-N-acetylsisomicin is isolated as the only product.

13-C-NMR-(D$_2$O/d-6-dioxane); rotamer mixture: 22.37/22.18 (CH$_3$CO); 177.13/176.76 (CO); 65.67/62.06 (C-3″); 21.59/21.36 (C(OH)-CH$_3$); and 32.97/30.35 (CH$_3$N).

EXAMPLE 18

1-N-Formylsisomicin 265 mg of the 2′,3,3″,6′-tetra-(N-o-nitrophenylsulphenyl)-sisomicin obtained according to Example 12 and 44 mg of p-nitrophenyl formate are dissolved in 1 ml of pyridine. The solution is left to stand at room temperature for 1 hour and evaporated in vacuo and the residue is taken up in 2 ml of methylene chloride. 7.5 ml of a methanolic H$_2$S solution, saturated at 0° C., and 0.75 ml of a methanolic hydrogen chloride solution, saturated at 20° C., are added to the solution, and after 1 minute the mixture is neutralised with concentrated ammonia solution. The mixture is evaporated in vacuo, the residue is digested with 10 ml of water and the digestion mixture is filtered. The filtrate is washed twice with ether, the aqueous phase is filtered over 12 ml of a basic ion exchanger in the OH$^\ominus$ form and the filtrate is evaporated. Yield: 102 mg of 1-N-formylsisomicin IR (KBr tablet):

band at 1,663 cm$^{-1}$.

| Tablet | Formulation 1 | | |
|---|---|---|---|
|  | 10 mg tablet | 25 mg tablet | 100 mg tablet |
| 1-N-Formyl-sisomicin | 10.50$^+$ mg | 26.25$^+$ mg | 105.00$^+$ mg |
| Lactose | 197.50 mg | 171.25 mg | 126.00 mg |
| Maize starch | 25.00 mg | 25.00 mg | 35.00 mg |
| Polyvinyl-pyrrolidone | 7.50 mg | 7.50 mg | 7.50 mg |
| Magnesium stearate | 2.50 mg | 2.50 mg | 3.50 mg |

$^+$ 5% excess

PREPARATION

A suspension of 1-N-formylsisomicin, lactose and polyvinylpyrrolidone is prepared and this is spray-dried. The maize starch and the magnesium stearate are added, the components are mixed and the mixture is pressed into tablets.

| Formulation 2 | |
|---|---|
| Ointment | |
| 1-N-Formylsisomicin | 1.0 g |
| Methylparaben U.S.P. | 0.5 g |
| Propylparaben U.S.P. | 0.1 g |
| Petrolatum | to 1,000 g |

PREPARATION (1) The petrolatum is melted;
(2) 1-N-formylsisomicin, Methylparaben and Propylparaben are mixed with about 10% of the molten petrolatum;
(3) The mixture is put into a colloid mill;

(4) The remaining petrolatum is added, whilst stirring, and the mixture is cooled until it becomes semi-solid. The product is filled into suitable containers.

| Injection solution | Formulation 3 per 2.0 ml phial | per 50 liters |
|---|---|---|
| 1-N-Formylsisomicin | 84.0 mg+ | 2,100.0 gm |
| Methylparaben, U.S.P. | 3.6 mg | 90.0 gm |
| Propylparaben, U.S.P. | 0.4 mg | 10.0 gm |
| Sodium bisulphite, U.S.P. | 6.4 mg | 160.0 gm |
| Disodium ethylenediamine-tetraacetate dihydrate | 0.2 mg | 5.0 gm |
| Water, U.S.P. q.s. | 2.0 mg | 50.0 liters |

+5% excess

EXAMPLE 19

(a) Penta-N-(o-nitrophenylsulphenyl)-sisomicin 38 g (0.2 mol) of o-nitrophenylsulphenyl chloride in 200 ml of dioxane, and 260 ml of 1 N NaOH are added to 13.84 g (20 mmols) of sisomicin sulphate in 100 ml of 1 N NaOH and 450 ml of freshly distilled dioxane so that the pH is adjusted to a value of 12–14. The precipitate is filtered off and dissolved in a $CH_2Cl_2$/water mixture and the methylene chloride phase is dried over $Na_2SO_4$.

Methylene chloride is added to the filtrate, the aqueous phase is discarded and the methylene chloride extract is dried over $Na_2SO_4$. The combined organic phases are evaporated to dryness and the residue is filtered over a column with a diameter of 8 cm containing 250 g of silica gel, first with methylene chloride and then with a methylene chloride/methanol mixture (97.5/2.5). After evaporating off the solvent from the filtrate, 22 g (91%) of penta-N-(o-nitrophenyl-sulphenyl)-sisomicin are obtained as an orangecoloured foam.

(b) 3"-N-(o-Nitrophenylsulphenyl)-sisomicin 160 ml of thiophenol are added to 16.0 g (13.2 mmols) of the penta-N-(o-nitrophenylsulphenyl)-sisomicin prepared under a) in 80 ml of absolute pyridine, after 1 hour the mixture is poured onto 500 ml of diethyl ether, the precipitate is taken up in methylene chloride/methanol (8/2) and the solution is filtered over silica gel (5.5 × 12 cm column, running agent methylene chloride/methanol = 8/2, increasing addition of the running agent mixture methanol/methylene chloride/20 percent strength ammonia = 4/2/1). After evaporating off the solvent from the red zone, 6.6 g (83%) of 3"-N-o-nitrophenylsulphenylsisomicin are obtained as a deep-red foam.

(c) 2′,3,3″,6′-Tetra-N-(o-nitrophenylsulphenyl)-sisomicin 4.4 g (15.0 mmols) of o-nitrophenylsulphenic acid p-nitrophenyl ester in 85 ml of methylene chloride are added to 3.0 g (5.0 mmols) of the 3″-N-o-nitrophenyl-sulphenyl-sisomicin prepared under b) in 5 ml of methanol and 45 ml of methylene chloride, the reaction mixture is immediately evaporated to dryness, the residue is taken up in methylene chloride and the solution is chromatographed on silica gel (5.5 × 30 cm column) with 200 ml of methylene chloride and then with methylene chloride/methanol (98/2). 500 fractions are collected, 2′,3,3″,6′-tetra-N-(o-nitro-phenylsulphenyl)sisomicin being obtained as an orange-coloured foam from the combined fractions 270 to 500.

(d) 1-N-Formylsisomicin 265 mg of the 2′,3,3″,6′-tetra-(N-o-nitrophenylsulphenyl)-sisomicin obtained according to c) and 44 mg of formic acid p-nitrophenyl ester are dissolved in 1 ml of pyridine. The solution is left to stand at room temperature for 1 hour and evaporated in vacuo and the residue is taken up in 2 ml of methylene chloride. 7.5 ml of a methanolic $H_2S$ solution, saturated at 0° C., and 0.75 ml of a methanolic hydrogen chloride solution, saturated at 20° C., are added to the solution, and after 1 minute the mixture is neutralised with concentrated ammonia solution. The mixture is evaporated in vacuo, the residue is digested with 10 ml of water and the digestion mixture is filtered. The filtrate is washed twice with ether, the aqueous phase is filtered over 12 ml of a basic ion exchanger in the OR$\theta$ form and the filtrate is evaporated. Yield: 102 mg of 1-N-formylsisomicin IR (KBr tablet):

band at 1,663 $cm^{-1}$.

EXAMPLE 20

3″-N-Ethyl-1,2′,3,6′-tetra-N-(o-nitrophenylsulfenyl)-sisomicin 34 g 1,2′,3,6′-tetra-N-(o-nitrophenylsulfenyl)-sisomicin are dissolved in 35 ml dimethylsulfoxid and 500 ml tetrahydrofuran. 8 ml 50 percent strength by weight aqueous acetic acid and 16 ml acetic aldehyde are added in consecution and the mixture is kept at room temperature for 30 minutes. Then 5.2 g sodium cyanoboronhydride are added and the mixture is stirred for 1 hour. Water is added and the reaction mixture is extracted with methylene chloride and the methylene chloride phase which contains the desired compound is washed with water. The methylene chloride solution is dried with sodium sulphate and the solvent is vaporized in vacuo. 33 g of the compound are obtained as a quellow amorphous precipitate.

$[\alpha]D^{22} = +91.5°$ (c = 1,0 $CHCl_3$)

EXAMPLE 21

3″-N-Ethyl-sisomicin

A solution of 32,6 g 3″-N-Ethyl-1,2′,3,6′-tetra-N-(o-nitrophenylsulfenyl)-sisomicin in a mixture of dichloromethan and methanol (4:1) are saturated with hydrogensulfide. Then hydrogenchloride is past in until the solution shows acid reaction. Water is added, the precipitate is filtered off, the aqueous phase is extracted twice with dichloromethan and the dichloromethan solution is evaporated in vacuo. After drying the residue in vacuo 18 g 3″-N-Ethyl-sisomicin are obtained in the form of the colourless hydrochloride.

$[\alpha]D^{22} = +129°$ (c = 1,0 in $H_2O$)

EXAMPLE 22

1,2′,6′-Tri-N-(o-nitrophenylsulfenyl)-sisomicin

To 9 g of sisomicin dissolved in 40 ml of methanol and 160 ml of dichloromethane are added dropwise 18 g of o-nitrophenylsulphenyl-p-nitrophenyl ester in 180 ml of dichloromethane. The solvent is evaporated in vacuo and the residue is chromatographed on silica gel with dichloromethane/methanol (95/5) with increasing amounts (at last 3% based on the dichloromethane/methanol mixture) of a mixture consisting of methanol/dichloromethane/20% aqueous ammonia (4/2/1).

5,1 g (28%) of 1,2',6'-tri-N-(o-nitrophenylsulfenyl)-sisomicin are obtained together with 5,8 g (27%) of 1,2',3,6'-tetra-N-(o-nitrophenylsulfenyl)-sisomicin identical with the product of example 10.

13-C-NMR (CDCl$_3$) of 1,2'6'-tri-N-(o-nitrophenylsulfenyl)-sisomicin:

δ=147.58 (C-5); 57.40 (C-1) 53.74 (C-3); 49.40 (C-6'); 38.38 (C-2) ppm.

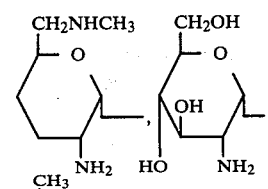

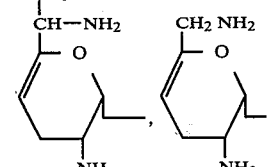

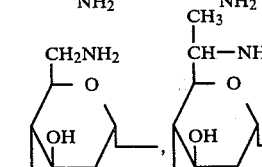

What is claimed is:

1. A member selected from the group consisting of a selectively protected diaminocyclitol and its pharmaceutically acceptable salts of the following formula (I),

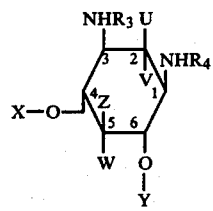

in which

X represents a radical of the formula

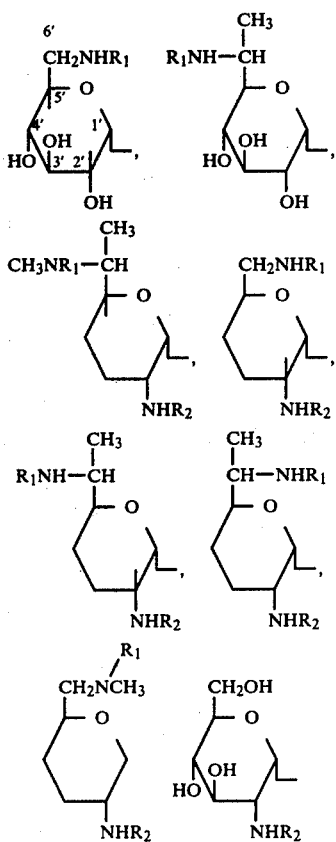

Y designates a radical of the formula

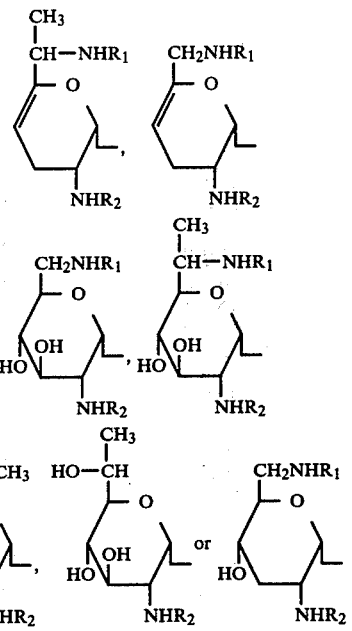

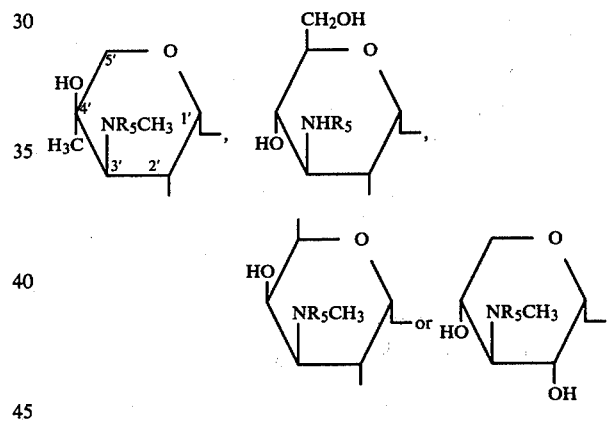

U, V and W are the same or different and each is hydrogen or hydroxyl; Z is hydrogen, hydroxyl or amino;

(1) R$_1$, R$_2$, R$_3$, R$_4$ and R$_5$ are each hydrogen or a radical —SR' with at least one being other than hydrogen, wherein R' is phenyl substituted by from one to three substituents each of which is nitro, C$_1$ to C$_4$-alkyl, C$_1$ to C$_4$-alkoxy, C$_1$ to C$_4$-alkoxycarbonyl, phenyl, by from 1 to 5 halogen atoms, diphenylmethyl or triphenylmethyl or (2) wherein R$_5$ is hydrogen and R$_1$, R$_2$, R$_3$ and R$_4$ are ethoxycarbonyl or acetyl.

2. A compound according to claim 1 which is derived from one of the antibiotics gentamicin A, gentamicin B, gentamicin B$_1$, gentamicin C$_1$, gentamicin C$_{1a}$, gentamicin C$_2$, gentamicin C$_{2a}$, gentamicin C$_{2b}$, gentamicin X$_2$, sisomicin, verdamicin, tobramicin, G-418, 66-40B, 66-40D, JI-20A, JI-20B, G-52, mutamicin 1, mutamicin 2, mutamicin 4, mutamicin 5 and mutamicin 6.

3. A compound according to claim 1 which is a compound of the formula (II)

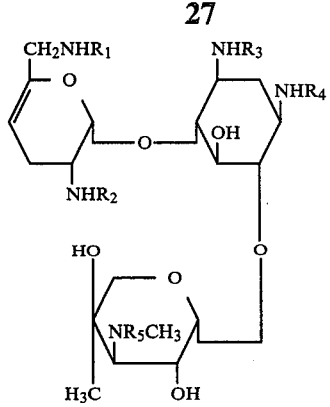 (II)

in which
R₁, R₂, R₃, R₄ and R₅ have the same meaning as defined hereinbefore in formula (I).

4. 1,2',3,6'-Tetra-N-ethoxycarbonyl-sisomicin.
5. 1,2',3,6'-Tetra-N-acetyl-sisomicin.
6. 1,2',3,6'-Tetra-N-(o-nitrophenylsulphenyl)-sisomicin.
7. 2',3,3'',6'-Tetra-N-(o-nitrophenylsulphenyl)-sisomicin.
8. 1,2',3'',6'-Tetra-N-(o-nitrophenylsulphenyl)-sisomicin.
9. 1,3,3'',6'-Tetra-N-(o-nitrophenylsulphenyl)-sisomicin.
10. 1,2',6'-Tri-N-(o-nitrophenylsulphenyl)-sisomicin.
11. A process for the production of a compound according to claim 1 in which a compound of the following formula (III) or an acid addition salt thereof

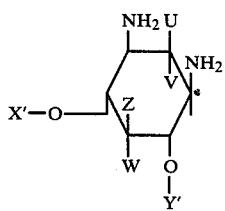 (III)

in which
U, V, W and Z have the same meaning as defined hereinbefore in formula (I)
X' represents a radical of the formula

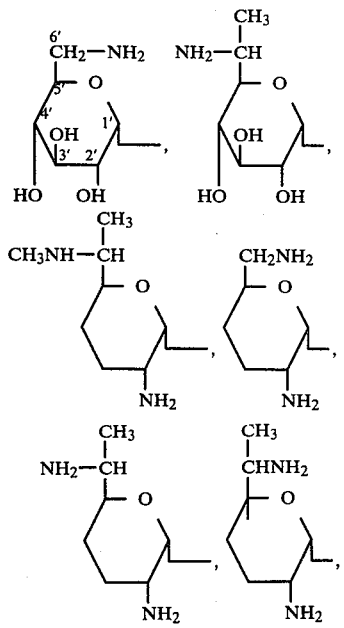

and

Y' designates a radical

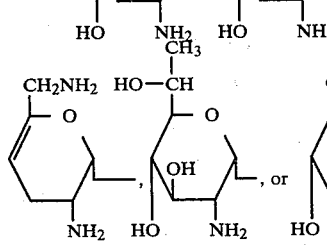

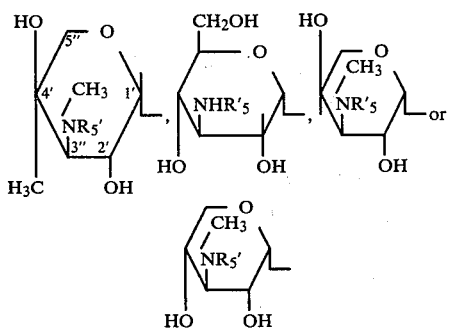

in which
R'₅ has the meaning indicated above for R₅, is reacted when one or more of R₁, R₂, R₃, R₄ and R₅ is a radical R'—S—, with at least one of R₁, R₂, R₃, R₄ and R₅ being hydrogen with from 3 to 4 equivalents of a compound of the formula (IV).

R'—S—G (IV)

in which R' has the same meaning as defined hereinbefore in R₁, R₂, R₃, R₄ and R₅ and
G designates halogen or a leaving group useful in a sulphenylation reaction.

12. A process according to claim 11 in which the reaction is carried out at from about −30° to +50° C.
13. A process according to claim 11 in which the reaction is carried out in the presence of a base.
14. A process according to claim 11 in which the reaction is carried out in the presence of an inert solvent optionally in the presence of water.

\* \* \* \* \*

-continued